United States Patent [19]
Provder et al.

[11] 4,344,709
[45] Aug. 17, 1982

[54] METHOD AND APPARATUS FOR PHOTOGONIOMETRIC ANALYSIS OF SURFACES

[75] Inventors: Theodore Provder, Olmsted Falls; Richard M. Holsworth, Westlake; Mark E. Koehler, Middleburg Heights, all of Ohio

[73] Assignee: SCM Corporation, Cleveland, Ohio

[21] Appl. No.: 147,854

[22] Filed: May 8, 1980

[51] Int. Cl.³ .................... G01N 21/55; G01N 21/47
[52] U.S. Cl. ................................ 356/445; 356/446; 356/448
[58] Field of Search ............... 356/445, 446, 447, 448

[56] References Cited

U.S. PATENT DOCUMENTS

| | | | |
|---|---|---|---|
| 2,388,727 | 11/1945 | Dench | 356/448 |
| 3,549,264 | 12/1970 | Christie | 356/446 |
| 3,916,168 | 10/1975 | McCarty et al. | 356/405 X |
| 3,999,864 | 12/1976 | Mutter | 250/227 X |

FOREIGN PATENT DOCUMENTS 642456  9/1950  United Kingdom ............... 356/446

OTHER PUBLICATIONS

"Journal of Paint Technology", vol. 40, No. 519; Apr. 1968; pp. 143-149, Billmeyer, Jr., et al.
"Color Engineering", May/Jun. 1971, pp. 31-36 Billmeyer, Jr., et al.
"Journal of Paint Technology", vol. 41, No. 539, Dec. 1969, pp. 647-653, Billmeyer, Jr., et al.
"Journal of Paint Technology", vol. 46, No 590, Mar. 1974, pp. 35-47, Tahan.
"Journal of Paint Technology", vol. 46, No. 590, Mar. 1974, pp. 48-57, Tahan et al.
"Journal of Paint Technology", vol. 46, No. 597, Oct. 1974, pp. 52-62, Tahan.
"Jocca", vol. 57, No. 12, Dec. 1974, pp. 403-406, Carr. Br. Polym. J., vol. 3, Nov. 1971, pp. 274-278, Quinney et al.
"Journal of Coating Technology", vol. 48, No. 613, Feb. 1976, pp. 53-60, Billmeyer, Jr., et al.
"Journal of Paint Technology", vol. 47, No. 602, Mar. 1975, pp. 52-59, Tahan et al.
"Reflectance Spectroscopy", Gustav Kortüm, Springer Verlag, 1969, pp. 4-71.

Primary Examiner—Vincent P. McGraw
Attorney, Agent, or Firm—Yount & Tarolli

[57] ABSTRACT

A method and apparatus for photogoniometric analysis of surfaces is disclosed. A photogoniometric instrument includes a light source (12) for providing a collimated beam of light illuminating a test surface (18). A light detector (20) is mounted for rotation about the point of intersection of the illuminating beam on the test surface. A motor (44) drives the detector through a range of reflectance angles, and a microcomputer (52) digitizes the detector output periodically, storing the digitized data words in its memory (68). These stored words define a photogoniometric curve (FIG. 2A) including a specular portion (FIG. 2D) and a nonspecular, or diffuse, portion (FIG. 2C). A host computer (62) receives the photogoniometric data from the microcomputer, deconvolutes the data into spectral and diffuse portions, and analyzes the two portions separately from one another. To accomplish this deconvolution, the host computer subtracts from the photogoniometric data the actual reflectance characteristic of a standard surface whose characteristic lacks the specular peak. This diffuse standard reflectance characteristic is stored in the host computer memory in the form of a mathematical equation which has been curve fitted to the actual reflectance characteristics of the diffused standard.

9 Claims, 12 Drawing Figures

METHOD AND APPARATUS FOR PHOTOGONIOMETRIC ANALYSIS OF SURFACES

BACKGROUND AND FIELD OF THE INVENTION

The present invention relates to methods and apparatus for analysis of surfaces, and more particularly to photogoniometric surface analysis.

In the development and manufacturing of surface coatings such as latex and oil based paints, varnishes, etc., a variety of analytical techniques are used for characterizing the surface morphology of the coatings. These techniques are useful in comparing different coatings, as well as in quantifying variations due to weathering and other effects.

One such analytical technique is photometric in nature and employs an instrument known as a "gloss meter." In this technique, a beam of collimated light is directed upon the surface under analysis at a selected incident angle, and intensity of light reflected at an angle of reflectance equal to the angle of incidence is measured. This light intensity reading is then used as a measure of the gloss characteristics of the surface being considered.

Other, photogoniometric, techniques are known wherein for a single incident angle, the intensity of reflected light is measured over a variety of reflectance angles so as to more clearly show the actual reflectance characteristics of the surface under study. The output of a photogoniometric instrument is a graph representing reflection intensity versus reflectance angle.

In general, such reflectance graphs display two major artifacts; a diffuse reflectance characteristic, and a spectral peak which is superimposed upon this diffuse reflectance characteristic. A mirror-like surface will display a very large, narrow spectral peak located at approximately the reflectance angle equal to the angle of incidence, while displaying a very low diffuse reflectance characteristic. A perfect diffuser, however, will essentially lack a spectral peak, hence the diffuse reflectance characteristic will predominate.

In analyzing such reflectance characteristic graphs, it is desirable that the spectral and diffuse portions be characterized independently of one another. Consequently, either an analysis technique must be devised which can analyze the two portions individually by examining the total reflectance characteristic as a whole, or else some method must be provided for deconvoluting the total reflectance characteristic into two separate characteristics, one carrying the spectral portion alone and another carrying the diffused portion alone.

Deconvolution of the reflectance curve could be easily done if the shape of either the spectral or diffuse portion were known with certainty. The unknown portion could then be easily isolated by merely subtracting the known spectral or diffuse portion from the total characteristic. It is known that a perfect diffuser in theory displays a reflectance characteristic which varies as the cosine of the reflectance angle. Furthermore, shape of this diffuse characteristic is independent of the incidence angle, although its magnitude may change. Consequently, if the diffuse portion of the curve were entirely ideal the deconvoluting of the two portions would be quite simple, requiring only that an appropriately scaled cosine curve be substracted from the total characteristics.

In practice, however, the actual diffuse portion of the curve will differ from an ideal cosine characteristic. The residual diffuse curve which will then appear in the spectral portion upon subtraction of the cosine curve will perturb the characterization of the spectral reflectance portion of the surface under analysis.

SUMMARY OF THE INVENTION

The present invention provides method and apparatus for photogoniometric analysis of material surfaces wherein the deconvolution of the photogoniometric reflectance curve is accomplished by subtracting out the actual diffuse characteristic of a standard surface, rather than an ideal cosine characteristic. Since an actual diffuse reflectance characteristic of a standard surface is used as the diffuse reflectance model, the subtraction of this diffuse model from the total reflectance characteristic results in the elimination of any residual diffuse portion from the spectral portion. Consequently, analysis of the spectral portion of the curve may be more readily accomplished.

In accordance with the present invention, a method is provided of analyzing the spectral reflectance characteristics of a test surface which includes the steps of illuminating the test surface with a collimated beam of light incident on the surface at a known angle, and measuring the reflectance characteristics of the test surface by measuring the intensity of light reflected from the surface at plural selected angles of reflectance. Also provided is the actual reflectance intensity versus reflectance angle characteristic of a standard surface whose characteristic substantially lacks a spectral peak. The difference between the reflectance characteristics of the test surface and the standard surface is analyzed and represents an analysis of the spectral reflectance characteristics of the test surface, since this difference represents the spectral reflectance characteristics of the test surface.

In the embodiment described, the diffuse reflectance standard used is a surface of titanium dioxide, produced by extensive weathering of a linseed oil based paint having a titanium dioxide pigment.

BRIEF DESCRIPTION OF THE DRAWINGS

The foregoing and other objects and advantages of the present invention will become more readily apparent from the following detailed description, as taken in conjunction with the accompanying drawings, wherein.

DETAILED DESCRIPTION

Figure 1:
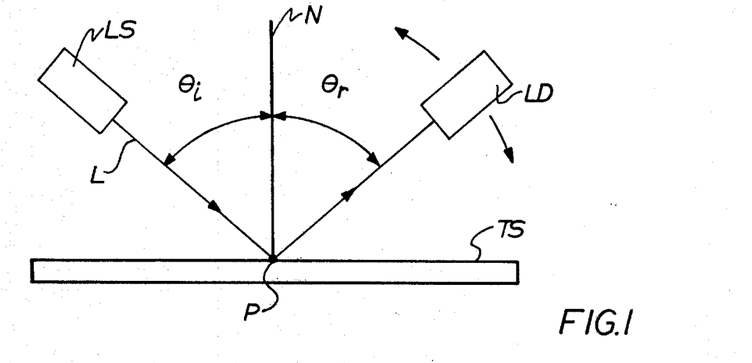
FIG. 1 is a conceptual representation of a photogoniometric instrument.

FIG. 1 illustrates in a largely conceptual manner the operation of a photometric surface analysis instrument. In the photometric analysis of a test surface TS, a light source LS is provided which generates a collimated beam of light L for illuminating the test surface TS. This light beam L is incident upon the test surface TS at an incident angle $\theta_i$, measured from the normal N to the surface TS. A light detector LD is provided at a selected reflectance angle $\theta_r$, again measured from the normal N to the surface TS, to detect the intensity of light reflected from the surface TS. In gloss meter instruments, this light detector LD is disposed at an angle of reflectance $\theta_r$, which is equal to the angle of incidence $\theta_i$. The gloss meter therefore provides a single value representing the magnitude of the light reflected from the surface TS at that selected angle.

Figure 2A:
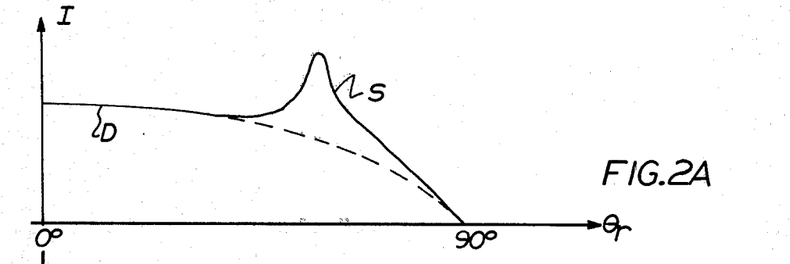
FIGS. 2A–2E are graphical representations of reflectance characteristics and portions thereof, useful in understanding the nature of the present invention.
Figure 2B:
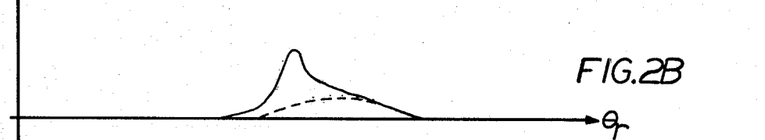

In a photogoniometric instrument, on the other hand, the light detector LD is mounted for rotation about the point P at which the optical axis of the light beam L intersects the test surface TS. As the light detector LD is rotated, the intensity measurments at the various reflectance angles $\theta_r$ are recorded. The results of a run on a photogoniometric instrument will be a chart relating the intensity of the reflected light I to the angle of reflectance $\theta_r$. Such a chart is illustrated in FIG. 2A.

In this graph it can be seen that the relationship between the intensity and reflectance angle is represented by two major components; a first portion D which generally follows a cosine curve and is commonly referred to as the diffuse reflectance characteristics of the surface, and a peak S which is superimposed on the diffuse portion D, and which is commonly referred to as the spectral reflectance peak. This spectral peak, when it is present in the reflectance characteristics of a test surface, will appear at an angle which is close to, but not necessarily equal to, the angle of incidence. Since the spectral peak may be offset from the reflectance angle equal to the incident angle, a gloss meter reading (which, it will be recalled, is only taken at the reflectance angle which is equal to the angle of incidence) may not accurately represent the peak reflected intensity.

As mentioned previously, to analyze this reflectance characteristic it is useful to deconvolute the curve into spectral and diffuse portions. One manner in which this could be done is to subtract a cosine curve (represented by the dotted portion of the graph of FIG. 2A) from the reflectance characteristics, with the cosine curve being normalized so that it had a value at a reflectance angle of zero which is equal to the intensity of the reflected light. If the test surface TS had a theoretically perfect diffuse reflectance characteristic, the result of this subtraction would be nothing more than the spectral peak, alone.

Surfaces requiring analysis, however, have reflectance characteristics whose diffuse portion does not exactly follow the theoretical cosine curve, hence the subtraction of a cosine curve leaves not only the spectral peak, but also a residual diffuse portion, which is known in the paint industry as "sheen." The presence of the sheen component in the spectral portion of the curve will influence the analysis of the spectral portion, in that it will affect such things as the intensity of the spectral peak, the broadening of the spectral peak, etc. It would therefore be desirable to provide some means of isolating the spectral peak such that the sheen component did not appear.

Figure 2C:
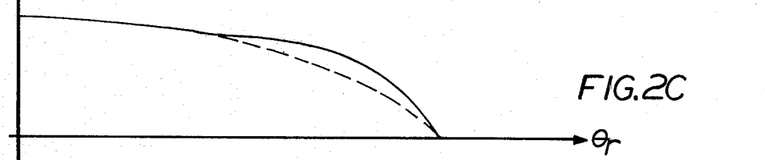

In accordance with the present invention, this is accomplished by subtracting, not the cosine characteristic of a perfect diffuser, but rather the actual reflectance characteristic of a surface which, however, does not have a spectral reflectance peak. This "diffuse standard" surface may, for example, be a conventional linseed oil based paint which includes a titanium dioxide pigment and which has been weathered for a thousand hours or longer on an Atlas "Weather-O-Meter." The resulting surface will be substantially entirely titanium dioxide, and will display a reflectance characteristic such as shown in FIG. 2C. It will be seen that this reflectance characteristic deviates from the perfect diffuser cosine characteristic (indicated by the dotted line), and lacks a spectral component.

Figure 2D:
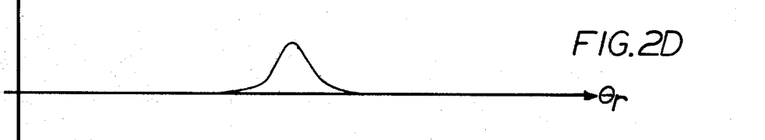

The extent of the sheen contribution in the diffuse standard reflectance characteristic will vary in dependence upon the incident angle $\theta_i$. More specifically, as the angle of incidence increases, the sheen contribution grows. In utilizing this diffuse standard characteristic to isolate the spectral peak from the characteristic of a test surface (FIG. 2A), a diffuse standard reflectance characteristic will be taken for an incident angle equal to the incident angle at which the test surface characteristic (FIG. 2A) was taken. The scale of the resulting graph (FIG. 2C) will then be adjusted so that the magnitude of the standard reflectance characteristic at a reflectance angle of zero is equal to the reflectance intensity of the test surface at the zero reflectance angle. To then deconvolute the reflectance characteristic of FIG. 2A, the normalized diffuse standard characteristic (FIG. 2C) is subtracted from it. Since the diffuse reflectance characteristic (including the sheen contribution) represents a close approximation of the actual diffuse portion of the test surface, the subtraction of one from the other leaves nothing more than the spectral peak, as shown in FIG. 2D.

Figure 2E:
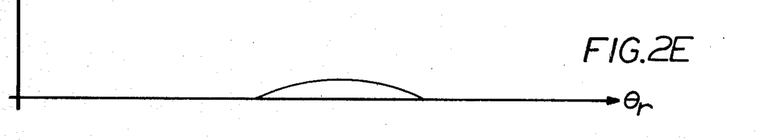

After separation in this manner, the spectral peak may be easily analyzed to determine such factors as its intensity, angle of occurrence of peak intensity, spreading, etc. If desired, the sheen portion of the characteristic may also be deconvoluted by subtracting a normalized cosine characteristic from the normalized diffuse reflectance characteristic of FIG. 2C. The result, shown in FIG. 2E, represents the extent to which the diffuse reflectance characteristic of the test surface deviates from the theoretical perfect diffuser.

It is presently preferred that the deconvolution and analysis of the various portions of the reflectance characteristic of a test surface be performed by a digital computer; the specific implementation which will now be described thus employs conventional computer hardware. It will be appreciated, however, that these goals could also be accomplished by means of an analog computer, by conventional dedicated electronic circuitry, or even by a purely mechanical device.

Figure 3:
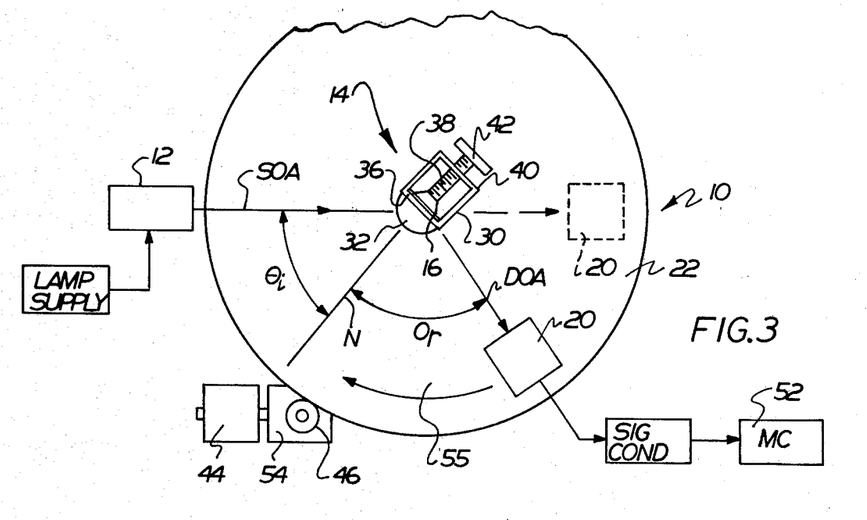
FIG. 3 is a plan view of a photogoniometric instrument such as may be used in carrying out the present invention.
Figure 4:
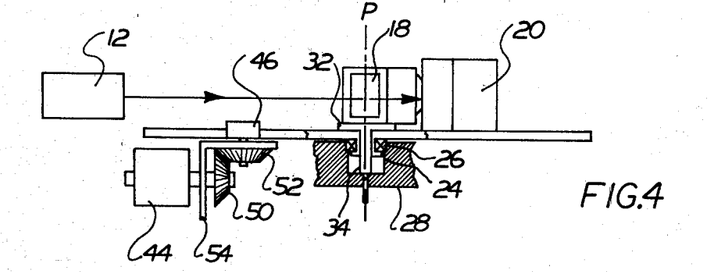
FIG. 4 is a side elevation view, partially cut away, of the photogoniometric instrument of FIG. 3.

FIGS. 3 and 4 illustrate in somewhat greater detail the actual mechanical arrangement of a photogoniometric instrument for deriving a reflectance characteristics curve such as have been described with reference to FIGS. 2A–2E. This photogoniometric instrument 10 includes a light source 12 which provides a collimated beam of light directed along an optical axis SOA. A sample holder 14 is provided which holds a sample 16 within the optical axis OA such that a surface 18 of the sample 16 is illuminated by the collimated beam of light provided by the light source 12.

A light detector 20 having a detector optical axis DOA is provided for viewing the illuminated test surface to determine the intensity of reflected light. The detector 20 is disposed relative to the test surface 18 such that the source optical axis SOA and detector optical axis DOA intersect surface 18 at a common point. Furthermore, the source 12, detector 20 and sample holder 14 are disposed relative to one another such that the source optical axis SOA, detector optical axis DOA, and the normal N to the test surface 18 all occupy a common plane.

The light detector 20 may be rotated within the common plane about the common intersection point on the test surface 18 so as to detect the intensity of reflected light at a variety of reflectance angles. To this end, the detector 20 is mounted upon a disk 22 which is coaxially mounted on the axis P about which the detector 20 must rotate. The disk 22 is attached to a hub 24 which is journaled for rotation in bearings 26 attached to a frame member 28.

The sample holder 14 includes a cube-shaped sample mount 30 which is attached to a table 32. The table 32 is integrally formed with a shaft 34 which is coaxially disposed along the axis P and which passes through a bore in the center of the hub 24 of the disk 22. The shaft 34 will normally be clamped to the frame member 28 so as to occupy a stationary, fixed orientation relative to the light source 12, which is also mounted upon the frame member 28. The clamp (not shown) may be released, however, so that the shaft 34 is free to rotate about the axis P, permitting the angle at which the light provided by light source 12 is incident upon the test surface 18 to be varied. There is adequate clearance between the shaft 34 associated with table 32 and the bore in the hub 24 associated with the disk 22 so that the disk 22 may be rotated independently of the table 32.

The sample mount 30 is attached to the table 32 at a location such that the inside surface of the front face 36 thereof is coincident with the axis P. This face 36 is partially open so as to expose the surface 18 of the sample 16 clamped within the sample mount 30. A vise clamp 38 is threadedly received within the rear face 40 of the sample mount 30 and is capped at its exposed end by a knurled knob 42 which may be turned to secure the sample 16 against the inside surface of the open face 36 of the sample mount 30. This insures that the surface of the test sample is disposed exactly on the axis P.

A high torque AC motor 44 is provided to automatically rotate the detector 20 at a fixed rate through a range of reflectance angles in the direction indicated by the arrow 55 in FIG. 3. This AC motor 44 is attached to a rim drive wheel 46 through bevel gears 50, 52 which are held in place by a bracket 54. The rim drive wheel 46 frictionally engages the rim of disk 22 for rotationally driving the disk 22 about the axis P.

Figure 5:
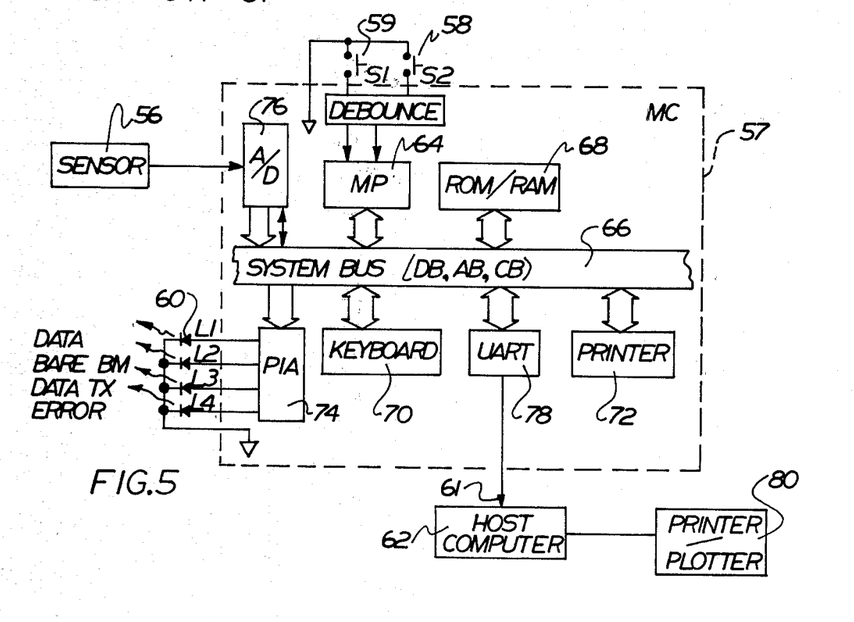
FIG. 5 is a broad block diagram of the circuitry utilized in gathering data from the photogoniometric instrument of FIGS. 3 and 4 and for analyzing that data.

FIG. 5 is a broad block diagram of the circuitry utilized to acquire and process the reflectance data generated by the photogoniometric instrument of FIGS. 3 and 4. In FIG. 5, the sensor 56, which represents both the detector and its associated signal conditioning circuits, is illustrated as providing an analog signal to a microcomputer, generally indicated at 57. This analog signal has a DC value which varies in accordance with the intensity of light impinging on the detector 20. Also interfaced with the microcomputer 57 are two control switches 58 and 59 and a series of indicator lights 60 (identified individually as L1-L4).

The microcomputer 57 controls the indicator lights 60 to advise the operator as to where in the data taking procedure the instrument is at any given time. The microcomputer 57 will transmit the data from the photogoniometric instrument to a host computer 62 over serial interface 61 for processing.

As illustrated in FIG. 5, the microcomputer 52 is controlled by a microprocessor 64 interconnected with a variety of peripheral devices by a system bus 66. This system bus includes an address bus AB, data bus DB, and control bus CB. Associated with the microprocessor 64 is a system memory 68, including read only memory (ROM) containing operating programs and random access memory (RAM) for storing data acquired from the photogoniometric instrument as well as header data entered by the operator through a keyboard 70. The memory 68 also interfaces with the microprocessor through the system bus 66.

Figure 6:
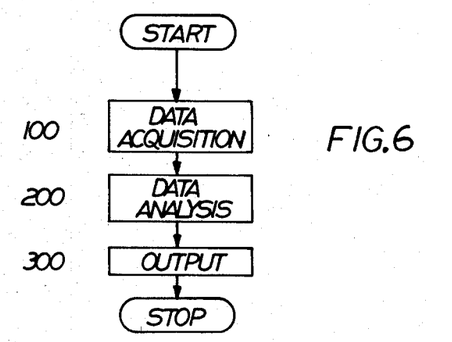
FIG. 6 is a flow chart broadly defining the sequence of operations performed by the microcomputer of FIG. 5.

FIG. 6 is a broad overview flow chart representing the basic operational steps involved in photogoniometric analysis with the instrument of FIGS. 3-5. As can be seen in this Figure, the analysis operation includes two major procedures: data acquisition and data analysis. The microcomputer 52 is used principally for the data acquisition and transmits the acquired data to a host computer 62, which performs the actual data analysis. These two procedures will be described separately with reference to FIGS. 7 and 8, respectively.

DATA ACQUISITION

Figure 7:
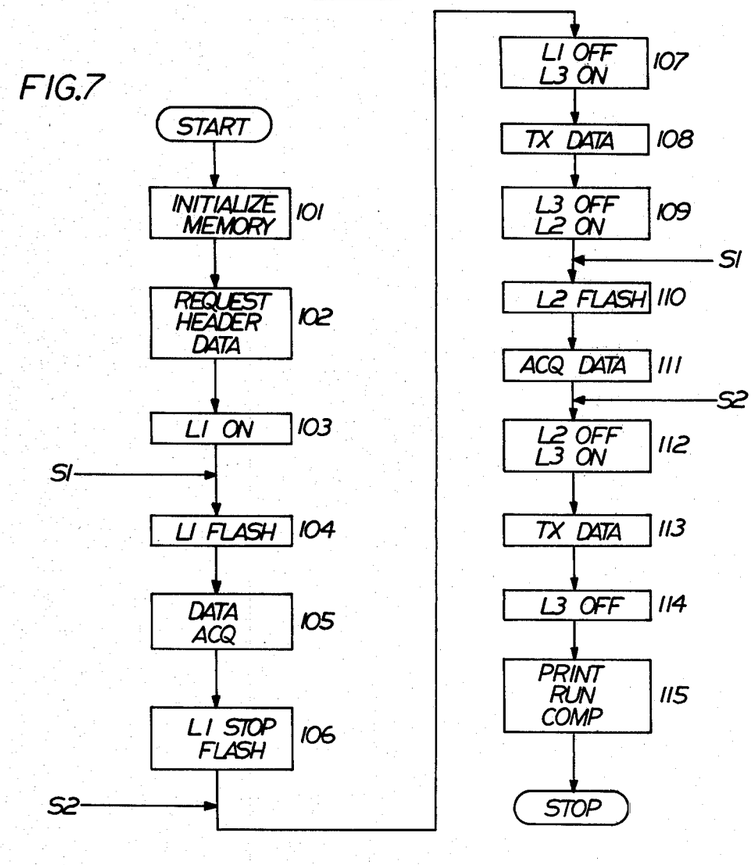
FIG. 7 is a flow chart illustrating the sequence of operations performed by the microcomputer of FIG. 5 during the taking of data; and, FIG. 8 is a block diagram identifying the sequence of operations performed by the minicomputer of FIG. 5 in reducing the photogoniometric data.

During the data acquisition procedure the operator enters appropriate header information into the microcomputer and initiates the rotation of the detector by turning on the motor 44. The microcomputer acquires the data and transmits it to the host computer for analysis. The procedure includes the following steps:

| STEP | FUNCTION |
| --- | --- |
| 101 | When the operator initially applies power to the instrument, the microprocessor 64 executes an initialization procedure wherein the memory is cleared, interrupt flags are set up, etc. |
| 102 | The microcomputer now prints out a header inquiry message to the operator via a printer 72 which, again, is connected to the microprocessor 64 through the system bus 66. In response, the operator enters appropriate header information into the keyboard 70. The microprocessor 64 may provide prompting instructions to the operator through the printer 72 in order to guide him through the entry of header information. In the illustrated embodiment, the operator sets the photogoniometric instrument to a selected incident angle, and then enters this incident angle into the microcomputer 52 via the keyboard 70. Also entered into the microcomputer is a starting reflectance angle, representing the reflectance angle beginning from which data will be taken |
| 103 | After all of the header information has been appropriately entered, the microcomputer 52 illuminates lamp L1 (lamps L2-L4 remain dark) through a conventional programmable interface adapter (PIA) 74. This advises the operator that the microcomputer is prepared to begin taking data. |

The operator then sets the detector 20 at an angle of reflectance which is greater than the starting angle entered into the computer, and turns on the motor 44 so that the detector 22 begins scanning over progressively smaller reflectance angles. The photogoniometric instrument of FIG. 3 includes angular graduations (not shown) along the disk 22 which are visible to the operator through an opening in the frame 28. These angular graduations indicate to the operator the angle between the normal N and the detector optical axis DOA. Upon energization of the AC motor 44, the reflectance angle gradually diminishes until a point is reached at which the angle of reflectance is equal to the angle from which data is to be taken by the microcomputer 52. As the detector passes through this angle the operator depresses a START button 54 (S1) to cause the microcomputer 52 to begin taking data.

| | |
|---|---|
| 104 | Upon the closure of switch S1, the microprocessor causes lamp L1 to flash, thereby indicating to the operator that data is being taken. |
| 105 | Thereafter, the output of the sensor 20 is regularly converted into digital words by means of an analog-to-digital converter 76, with the resulting digital words being transferred into sequential locations in the memory 68. Each word represents a singal data point on the photogoniometric curve for the test sample. |

The rate of rotation of the detector 20 is fixed by the speed of the motor 44 which, in turn, is constant since the motor 44 is synchronous with the AC powerline. The rate of taking samples of the sensor output is related to this speed. In the described embodiment, one sample is taken for each degree of rotation of the detector 20.

| | |
|---|---|
| 106 | After the microcomputer 57 determines (by subtracting one degree from the starting angle for each sample taken) that the detector 20 has reached the normal N to the test surface 18, data light L1 is caused to cease flashing, thus indicating to the operator that data taking is completed. |
| 107 | The operator then closes stop switch 52 (S2) to enable the transmission of data to the host computer. In response, the microprocessor turns lamp L1 off the lamp L3 on, indicating that data transmission is in progress. |
| 108 | The microcomputer 52 transmits the acquired photogoniometric data along with the associated header information to the host computer 62 over serial interface 61. A conventional universal asynchronous receiver/transmitter (UART) 78 is utilized for this communication function. |
| 109 | After data transmission is complete, lamp L3 is extinguished and lamp L2 is illuminated by the microprocessor through the PIA 74, indicating to the operator that he should now set the photogoniometric instrument to scan the bare beam. |

To scan the bare beam, the operator first removes the sample mount 30 from the table 32 so that the detector may now be positioned in the direct line-of-sight of the light source (as indicated by the detector position shown in broken lines). The operator then positions the detector 20 so that the motor 44 will cause it to rotate through the direct line-of-sight position and to thus scan the bare beam, which now passes unimpeded into the detector because of the removal of the sample mount.

| | |
|---|---|
| 110 | Somewhat before the detector 20 reaches the bare beam, the operator again depresses the start switch 54 (S1), causing the microprocessor to start lamp L2 flashing. |
| 111 | The microprocessor then begins regularly taking bare beam samples via the A/D converter 76. |
| 112 | After the detector 20 passes beyond the bare beam, the operator depresses S2, advising the microcomputer that the scanning of the bare beam has been completed. The microcomputer extinguishes lamp L2 and turns lamp L3 on. |
| 113 | Thereafter the microprocessor transmits the bare beam data, again including the header data, to the host computer 62 via the UART 78. |
| 114 | Upon completion of the transmission of data the lamp L3 is extinguished. |
| 115 | Finally, the microcomputer advises the operator the run has been completed by printing an appropriate message upon the printer 72. |

DATA ANALYSIS

Figure 8:
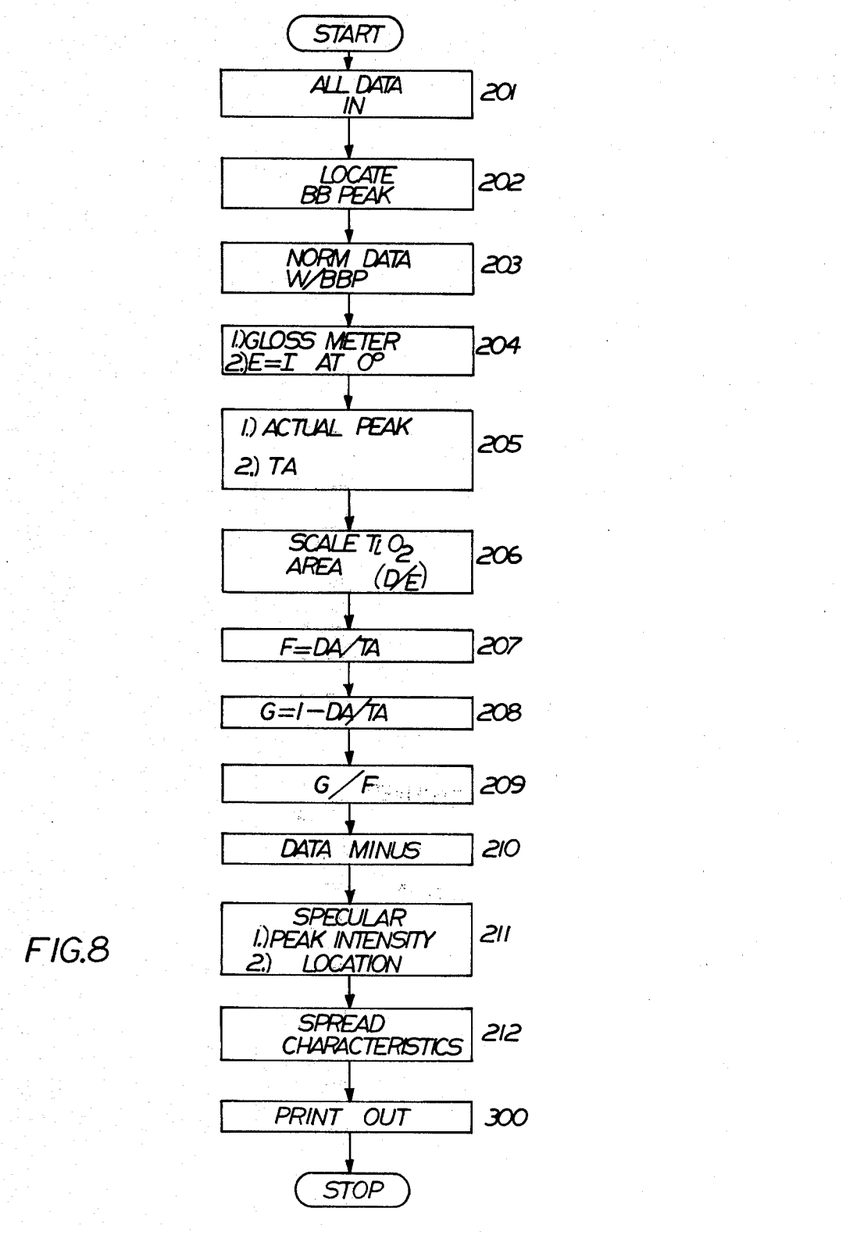

The data analysis procedure 200 is performed by the host computer 62, and generally involves the deconvolution of the photogoniometric data and the analysis of this deconvoluted data.

The host computer 62, in accomplishing this analysis, utilizes stored data representing the actual reflectance characteristics of a diffuse standard at each of a number of standard incident angles. This data will have been acquired on a previous occasion and will have been reduced to a form compatible for efficient storage in the host computer's memory. In the embodiment being described, this is accomplished by normalizing the diffuse standard reflectance curve and curve fitting an equation of the form $I = \cos\theta + A + B\theta + C\theta^2$ to the normalized curve, where I is intensity of reflected light, $\theta$ is the reflectance angle at which that intensity was measured, and A, B, and C are curve fitting coefficients selected to match the equation to the normalized curve of a reflectance characteristic at a given incident angle. Normalization of the diffuse standard data is done by dividing the intensity data by the intensity measured at a zero reflectance angle. The resulting normalized curve has a value of unity at a zero reflectance angle.

Since the reflectance curve will be different for different angles of incident light, the coefficients A, B, and C will also be different for different incident angles. These various different coefficient values are stored in the memory of the host computer in the form of a table relating incident angle to associated values of A, B, and C. Stored in this table with each set of A, B, C values is another value D representing the area under the corresponding diffuse standard reflectance curve. The appropriate A, B, C and D values to be used in an analysis are retrieved by utilizing the incident angle used in the taking of the photogoniometric test data (and entered into the microcomputer 52 by the operator as part of the header) to access the table of values.

The data analysis procedure includes the following steps:

| STEP | FUNCTION |
|---|---|
| 201 | Upon the receipt of the bare beam data, the host computer checks to verify that the photogoniometric test data is also stored within memory. Upon verification of this, the data analysis program (steps 202–212) is called and executed. |
| 202 | The bare beam data is examined to locate the bare beam peak. In this step the host computer scans the bare beam peak to find (1) the peak intensity of the |

| STEP | FUNCTION |
|------|----------|
|  | bare beam, and (2) the spread of the bare beam peak, i.e., the width of the peak. |
| 203 | The photogoniometric data of the test sample is normalized by dividing each of the sampled intensity data values by the value determined in part (1) of step 202 representing the peak intensity of the bare beam. The normalized data resulting from this step is thus expressed in terms of percent of bare beam peak. |
| 204 | In this step the host computer determines two factors: (1) a gloss meter reading corresponding to the intensity of reflected light at the reflectance angle which is equal to the angle of incidence (this is done by reading from the stored normalized data the normalized intensity value for the angle of reflectance equal to the angle of incidence; the correct data point is identified by determining the difference between the starting angle and the desired angle of reflectance, multiplying the result by the number of data points taken per degree of detector movement to get a product P corresponding to the number of data points between the starting angle and the desired angle, and using the $P^{th}$ data point as the gloss meter reading), and (2) the reflectance intensity E at a zero reflectance angle (determined similar to the gloss meter reading except that the data point is taken at a zero reflectance angle). |
| 205 | In this step the host computer determines: (1) the actual peak reflectance value (determined by scanning through the normalized data point by point to find the maximum value), and (2) the total area under the normalized reflectance characteristic (determined by adding together all of the normalized reflectance data values). |
| 206 | The stored value D representing the area under the appropriate diffuse standard curve is scaled in accordance with (i.e., multiplied by) the scale factor E determined in part (2) of step 204. |
| 207 | The ratio F of the area under the diffuse part of the curve to the total area under the entire curve is determined by dividing the scaled diffuse area DA (from step 206) by the total area TA under the photogoniometric curve, as determined in step 205. |
| 208 | The ratio G of spectral area to the total area is determined by subtracting the value determined in step 207 (DA/TA) from unity. |
| 209 | The result G of step 208 is divided by the result F of step 207 to provide a ratio of spectral area to diffuse area of the photogoniometric sample data. |
| 210 | For each of the values of normalized photogoniometric sample data, a corresponding value of the scaled diffuse standard data is determined and subtracted, so that the resulting data contains only the spectral peak. The corresponding value of the scaled diffuse standard is calculated by evaluating the equation $E[Cos\theta + A + B\theta + C\theta^2]$, where E is a scale factor corresponding to the value determined in part (2) of step 204; A, B, and C are stored values which match the equation to the actual curve of the diffuse standard as determined for an incident angle equal to the one used when the photogoniometric data was taken; and $\theta$ is the reflectance angle at which that data value was taken. |
| 211 | The resulting specular peak data is scanned to determine (1) the peak intensity of the specular peak, and (2) the location of the mean specular peak, in reflectance angle degrees. |
| 212 | The spread characteristics of the specular peak are determined, including (1) skewness, (2) kurtosis, and (3) broadening of the specular peak relative to the bare beam. |

After completing step 212, The calculated data together with a graph of the photogoniometric data and the specular peak are provided to the operator by any conventional printer or plotter 80.

The printed data includes the following:

| GLOSS MEASUREMENTS | |
|---|---|
| Gloss factor - ratio of areas, spec/diff | (From Step 209) |
| Reflectance equivalent to gloss meter reading | (From Step 204(1)) |
| TRACE STATISTICS | |
| Peak reflectance (percent) | (From Step 205(1)) |
| Total area under the curve | (From Step 205(2)) |
| SPECULAR PEAK | |
| Specular area as a percent of total | (From Step 208) |
| Maximum intensity of Specular reflection | (From Step 211(1)) |
| Shift of peak from incident angle | (From Step 211(2)) |
| Beam Spreading | (From Step 212) |
| DIFFUSE CHARACTERISTIC | |
| Diffuse area as a percent of total | (From Step 207) |
| Maximum intensity of diffuse reflection | (From Step 204(2)) |

As stated previously, this data may then be used to analyze weathering effects, manufacturing variances, etc., as well as to quantify differences between various test surfaces. Moreover, since these photogoniometric characteristics are related to the morphology of the surface under analysis, they may be used as a tool for morphological analysis.

Although the invention has been described with respect to a preferred embodiment, it will be appreciated that various rearrangements and alterations of parts may be made without departing from the spirit and scope of the invention, as defined in the appended claims. For example, surfaces other than titanium dioxide, such as barium sulfate or magnesium oxide surfaces, could be used as the diffuse standard.

What is claimed is:

1. A method of analyzing the specular reflectance characteristics of a test surface comprising the steps of:
   illuminating said test surface with a collimated beam of light incident on said surface at a known angle,
   measuring the reflectance characteristics of said test surface by measuring the intensity of light reflected from said surface at plural selected angles of reflectance,
   providing a mathematical equation relating reflectance intensity to reflectance angle for a standard surface whose reflectance characteristic substantially lacks a spectral peak, and
   analyzing the difference between the reflectance characteristics of said test surface and said mathematical equation, said difference representing the spectral reflectance characteristic of said surface.

2. A method as set forth in claim 1, wherein said analyzing step comprises the steps of scaling said mathematical equation so that said scaled equation defines a charcteristic which substantially corresponds to the non-spectral portion of the reflectance characteristic of said test surface, subtracting said scaled equation from said reflectance characteristic of said test surface to provide a characteristic essentially representing only the spectral reflectance characteristic of said test surface, and analyzing said spectral reflectance characteristic.

3. A method as set forth in claim 2, wherein said step of scaling comprises the step of scaling the mathematical equation for said standard surface such that the scaled equation evaluated at a substantially zero reflectance angle is substantially the same as the measured reflectance intensity of said test surface at said substantially zero reflectance angle.

4. A method as set forth in claim 1, wherein said step of providing said mathematical equation comprises the step of providing a mathematical equation of the form $I=K[\cos\theta + f(\theta)]$ where I is reflectance intensity, $\theta$ is reflectance angle, K is a proportionality factor, and $f(\theta)$ is a function selection to match the difference between the actual reflectance characteristic of said standard surface and the theoretical characteristic of a perfect diffuse reflector.

5. A method as set forth in claim 4, wherein $f(\theta)$ varies with the angle at which light was incident on said standard surface when said reflectance characteristic thereof was derived, and wherein said providing step further comprises the step of providing the $f(\theta)$ associated with the incident angle corresponding to the angle at which light was incident on said test surface when said measuring step was performed.

6. A method as set forth in claim 5, wherein said step of providing the $f(\theta)$ associated with the incident angle corresponding to the angle at which light was incident on said test surface comprises the steps of providing a general mathematical function $f(\theta)$ of the form $A+B\theta+C\theta^2$, where A, B, and C are coefficients whose values vary with said incident angle, and providing specific values for the coefficients A, B, and C in accordance with the angle at which light was incident on said test surface when said measuring step was performed.

7. A method as set forth in claim 1, wherein said step of providing a mathematical equation comprises the steps of illuminating said standard surface with a collimated beam of light incident on said surface at a known angle, measuring the reflectance characteristics of said standard surface by measuring the intensity of light reflected from said surface at plural selected angles of reflectance, matching a mathematical equation to said reflectance characteristic, and providing said mathematical equation as an indication of the actual reflectance characteristics of said standard surface.

8. A method as set forth in claim 7, wherein said step of matching a mathematical equation comprises the step of selecting values for coefficients A, B, and C such that the function $I=K[\cos\theta+A+B\theta+C\theta^2]$ closely matches said reflectance characteristic, where I is reflectance intensity and $\theta$ is reflectance angle.

9. A method as set forth in claim 1 wherein said standard surface comprises substantially $TiO_2$.

* * * * *